United States Patent [19]

Börner et al.

[11] Patent Number: 4,970,314

[45] Date of Patent: Nov. 13, 1990

[54] PROCESS FOR THE PREPARATION OF 2-BROMO-8-ERGOLINYL COMPOUNDS

[75] Inventors: Helmut Börner; Gregor Haffer; Gerhard Sauer, all of Berlin, Fed. Rep. of Germany

[73] Assignee: Schering Aktiengesellschaft, Berlin and Bergkamen, Fed. Rep. of Germany

[21] Appl. No.: 668,344

[22] Filed: Nov. 5, 1984

[30] Foreign Application Priority Data

Nov. 3, 1983 [DE] Fed. Rep. of Germany .... 33400253

[51] Int. Cl.$^5$ .................. C07D 457/04; C07D 457/06; C07D 498/12
[52] U.S. Cl. ..................................... 544/346; 546/68; 546/69
[58] Field of Search .................... 260/694; 546/67, 68, 546/69; 544/346

[56] References Cited

U.S. PATENT DOCUMENTS

| | | | |
|---|---|---|---|
| 4,219,555 | 8/1980 | Ručman et al. | 544/346 |
| 4,352,909 | 10/1982 | Barda et al. | 525/155 |
| 4,356,305 | 10/1982 | Szantag et al. | 546/51 |
| 4,609,731 | 9/1986 | Jurgec et al. | 544/346 |

OTHER PUBLICATIONS

Radhakrishnamurti et al., Tetrahedron Letters, No. 54, pp. 4765–4767 (1969).
Berde et al, Ergot Alkaloids and Related Compounds, pp. 40–41 (1978).
Hart et al., "The Reaction of Bromine with Cyclohexene in Carbon Tetrachloride . . . ," J. Chem. Soc. Perkin trans II (1983), pp. 1087–1092.
Radhakrishnamurti et al. ". . . Catalytic Effect of Acetic Acid on Reactions–with Hydrogen Halide," *Chem. Abst.* 72:54437c.
Troxter et al., "Substitutionen am Ringsystem der Lysergsaure . . . ," Helv. Acta. XL (1957), pp. 2160–2170.

*Primary Examiner*—Cecilia Shen
*Attorney, Agent, or Firm*—Millen, White & Zelano

[57] ABSTRACT

2-bromo-8-ergolinyl compounds of the formula

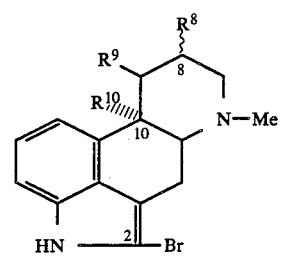

wherein
$R^8$ is $NH_2$, $NH-CONEt_2$, $CONH_2$,

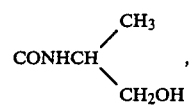

and

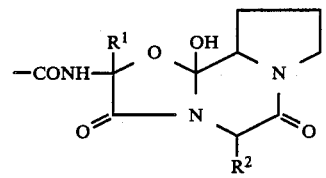

wherein
$R^1 = C_{1-4}$-alkyl and
$R^2 = C_{1-4}$-alkyl and benzyl,
$R^9$ and $R^{10}$ each mean hydrogen or, together, a bond, and the substituent $R^8$ can be in the α- or β- position, and their acid addition salts, can be prepared from corresponding 8-ergolinyl compounds and their acid addition salts by bromination with elemental bromine in the presence of hydrogen bromide in a halogenated hydrocarbon.

18 Claims, No Drawings

PROCESS FOR THE PREPARATION OF 2-BROMO-8-ERGOLINYL COMPOUNDS

BACKGROUND OF THE INVENTION

This invention relates to a novel process for the preparation of 2-bromo-8-ergolinyl compounds.

2-bromo-8-ergolinyl compounds are important drugs from the series of ergot alkaloids such as, for example, the known bromocriptine for the treatment of hyperprolactinemia (H.R. Schneider et al. Experientia 33 (1977) 1412) or 2-bromolisuride (EPA 0056 358). However, they can also be used as intermediates for the production of pharmacologically active ergot alkaloids, e.g., 9,10-didehydro-6-methylergoline-8α-amine according to the procedure of U.S.S.N. 452,521 and 9,10-didehydro- 6-methylergoline-8α-carboxylic acid amide according to the procedure described in U.S.S.N. 415,612 for the production of bromerguride.

Bromination methods for ergot alkaloids have been known for some time (see, for example, F. Troxler and A. Hofmann, Helv. Chim. Acta 40 : 2160 [1957]). According to this classic process, moderate yields of lysergic acid derivatives are obtained under heating with 1.2–1.5 molar equivalents of N-bromosuccinimide in dioxane, forming the corresponding 2-bromo compounds. Numerous suitability tests have been conducted in the past on a great variety of brominating agents, such as dioxane dibromide, N-bromocaprolactam, or N-bromophthalimide (for example, DOS 1,926,045).

Other selective brominating agents for this purpose are, for example, the bromine addition complexes 2-pyrrolidone hydrotribromide (DOS 2,752,532) and 3-bromo-6-chloro-2-methylimidoazo[1,2-b]pyridazine hydrotribromide (DOS 2,938,313).

All of these brominating methods have the disadvantage that, on the one hand, the yields of desired bromination product are not quantitative and, on the other hand, the bromination product frequently requires a technically rather expensive procedure for separating it from the corresponding carrier compounds formed from the brominating reagents employed and present in the reaction mixture.

SUMMARY OF THE INVENTION

Accordingly, it is an object of the present invention to make available a selective brominating method for 8-ergolinyl compounds providing almost quantitative yields and simplifying the processing of the bromination product from a technical viewpoint.

Upon further study of the specification and appended claims, further objects and advantages of this invention will become apparent to those skilled in the art.

These objectives of this invention have been attained by conducting the brominating reaction with elemental bromine in the presence of hydrogen bromide in a halogenated hydrocarbon as the solvent.

More particularly, this invention relates to a process for the preparation of 2-bromo-8-ergolinyl compounds of Formula I

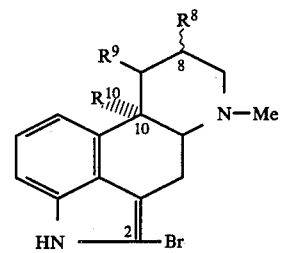

wherein

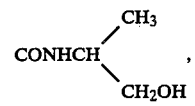

$R^8$ is $NH_2$, $NH-CONEt_2$, $CONH_2$,

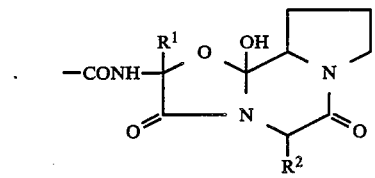

Wherein
$R^1 = C_{1-4}$-alkyl and
$R^2 = C_{1-4}$-alkyl or benzyl,
R9 and R10 each mean hydrogen or, together form an additional bond and the substituent R8 can be in the α-or β-position, and their acid addition salts, by bromination of corresponding 8-ergolinyl compounds unbrominated in the 2-position and their acid addition salts. The bromination is conducted with elemental bromine in the presence of hydrogen bromide in a halogenated hydrocarbon as the solvent, and, if desired, subsequently producing the acid addition salt in a conventional way using the normal procedures of neutralization reactions.

DETAILED DESCRIPTION OF THE INVENTION

Examples of suitable halogenated hydrocarbons include methylene chloride, carbon tetrachloride, chloroform, 1,2-dichloroethane, 1,2-trichlorotrifluoroethane, and, in particular, methylene dichloride.

The reaction of this invention is suitably performed under a protective gas, such as nitrogen or a noble gas atmosphere, and at temperatures below room temperature (e.g., <25° C.), preferably at 0–15° C., i.e., at temperatures which are obtained with external ice water cooling, for a period of 20–150 minutes.

Examples for salts (starting material and/or product) include the hydrogen maleate, hydrogen phosphate, methanesulfonate, hydrochloride, hydrobromide, hydrogen sulfate, and the tartrate. Suitable alkyl moieties for the above are methyl, ethyl, n- or iso-propyl or a butyl group.

Approximately equimolar amounts, preferably using a small excess, are employed of the elemental bromine and the hydrogen bromide. Accordingly, 1.0–1.1 molar equivalents of bromine and hydrogen bromide are utilized, based on the 8-ergolinyl compound. Typically, the ergolinyl starting material is used in a concentration of 0.01–0.2 mole/l of solvent. The hydrogen bromide is, for this purpose, suitably diluted in glacial acetic acid; in this connection, an approximately 33% strength solution of hydrogen bromide in glacial acetic acid proved to be advantageous. The reaction product can subsequently be separated from the reaction mixture by a simple technical step, such as extraction and crystallization.

The results of the process of this invention are surprising insofar as the work by Troxler and Hofmann (loc. cit.) did, in fact, also utilize molecular bromine, obtaining very rapidly a mixture of various superbrominated compounds, which mixture moreover contained also considerable quantities of decomposition products from which uniform derivatives could be separated only with difficulties. Therefore, it was impossible to foresee that a selective halogenation in the 2-position of the 8-ergolinyl compounds could be performed when brominating with molecular bromine in the presence of an equal amount of hydrogen bromide in a halogenated hydrocarbon as the solvent, arriving at a reaction mixture that can be worked up with relative ease.

Bromination takes place regioselectively in the 2-position. There is no epimerizing in the 8-position. As a result, correspondingly high yields of the desired 2-bromo-8-ergolinyl compounds are obtained.

All starting materials are known and/or readily preparable from known or readily preparable starting materials, e.g., V. Zikan et al., Pharmazie 23 (1968) 147; A. Mofmann, Die Mutterkornalkaloide, F. Enke Verlag, Stuttgart 1964, page 34; J. Rutschmann et al. in B. Berde and H.O. Schild (Edts.), Ergot Alkaloids and Related Compounds, Springer Verlag Berlin-Heidelberg-N.Y. 1978, page 35.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

Under a nitrogen atmosphere, 22.73 g of 3-(9,10-didehydro-6-methyl-8a-ergolinyl)-1, 1-diethylurea, hydrogen maleate (=lisuride hydrogen maleate), 50 mmol, is suspended in 500 ml of methylene dichloride. Under cooling of the batch with ice water and under agitation, 9.48 ml of hydrogen bromide in glacial acetic acid (33% strength, 55 mmol) is added dropwise within one minute. The compound is dissolved while being added. The reaction solution turns a green color. Subsequently, 2.68 ml of bromine (52.5 mmol), dissolved in 500 ml of methylene dichloride, is added uniformly during a period of 2 hours and under further cooling; the mixture is stirred for 10 minutes, diluted with 1000 ml of methylene dichloride, then combined with 750 ml of 5% strength sodium bicarbonate solution, and allowed to warm up to room temperature within 30 minutes under agitation. The methylene dichloride phase is separated, the aqueous phase is extracted three times with respectively 500 ml of methylene dichloride. The combined methylene dichloride solutions are washed once with 500 ml of water, and the washing water is reextracted with 250 ml of methylene dichloride. The methylene dichloride solution, dried over sodium sulfate, is evaporated under vacuum and made to crystallize for 4 hours at $-15°$ C. The precipitate is vacuum-filtered, washed with 20 ml of methylene dichloride, and dried under vacuum, thus obtaining 22.90 g of crude product, $[\alpha]_D^{25}+244.61°$ [c=0.5, pyridine], of which 22.80 g is dissolved in 2000 ml of methylene chloride and stirred for 30 minutes with 34 g of silica gel. The solid matter, passed through a porous plate, is washed in succession with 1000 ml of methylene dichloride and 1000 ml of methylene dichloride - methanol (97 : 3), and evaporated separately. The residue is taken up in 179 ml of ethanol and combined with 119 ml of water under agitation. The precipitate is suctioned off and washed with 15 ml of a cold ethanol- water mixture (60 : 40) and dried. Yield: 11.51 g of 2-bromolisuride $[\alpha]_D^{25}=305.6°$ [c=0.5, pyridine].

The mother liquor is concentrated under vacuum, then extracted three times with respectively 50 ml of methylene dichloride under shaking, and evaporated to dryness. The residue is eluted, together with the methylene dichloride - methanol residue, on 250 g of silica gel with 2400 ml of methylene dichloride - methanol 97 : 3), evaporated, dissolved in 82.5 ml of ethanol, and worked up as described above after addition of 55 ml of water. Yield: another 6.16 g of 2-bromolisuride; $[\alpha]_D^{25}=304.4°$ [c=0.5, pyridine]. Total yield: 17.67 g (85.0 % of theory); mp: 133–140° C. (decomposition); $[\alpha]_D^{25}=305.2°$ (c=0.5, pyridine).

In the same way, with the use of the free 3-(9,10-didehydro-6-methyl-8α-ergolinyl)-1, 1-diethylurea and the 3-(9,10-didehydro-6-methyl-8α-ergolinyl)-1,1-diethylurea hydrobromide (mp 221° C. [decomposition]; $[\alpha]_D^{25}=277.2°$ [c=0.5, pyridine]) as starting compounds, the product is 2-bromo-3-(9,10-didehydro-6-methyl-8-ergolinyl)-1,1-diethylurea in a yield of 84.3% of theory ($[\alpha]_D^{25}=-305°$ ]c=0.5, pyridine]) and of 81.5% of theory ($[\alpha]_D^{25}=304.7°$ [c=0.5, pyridine]), respectively.

EXAMPLE 2

417.4 mg of 2-bromolisuride (1 mmol) is dissolved in 8.5 ml of ethanol. Under an inert gas atmosphere, 0.189 ml of hydrogen bromide in glacial acetic acid (33% strength, 1.1 mmol) is added dropwise thereof within one minute at room temperature; the mixture is stirred for another 10 minutes and allowed to crystallize under ice water cooling. The filtered-off precipitate is rewashed with a small amount of ice-cold ethanol, thus obtaining 433.5 mg of 2-bromolisuride, hydrobromide (87.0% of theory), mp 225–230° C. (decomposition); $[\alpha]_D^{25}=311.8°$ (c=0.5, pyridine).

EXAMPLE 3

Analogously to Example 1, the following products are obtained:
from 3-(9,10-didehydro-6-methyl-8β-ergolinyl)-1,1-diethylurea:
  3-(2-bromo-9,10-didehydro-6-methyl-8β-ergolinyl)-1,1-diethylurea; 74.8% yield, $\alpha=+104.1°$ (c=0.5, pyridine) $=+45.3°$ (c =0.5, methanol) hydrobromide; 84.0% yield, $[\alpha=39.2°$ (c =0.5, methanol) $=+55.0°$ (c =0.5, pyridine);
from 1,1-diethyl-3-(6-methyl-8α-ergolinyl)urea:
  3-(2-bromo-6-methyl-8α-ergolinyl)-1, 1-diethylurea; 83.1% yield, mp 189-200° C. (decomposition), $[\alpha]_D^{25}=33.3°$ (c=0.5, pyridine), hydrobromide;

83.0% yield [α]$_D^{25}$=+60.6° (c=0.5, pyridine);
from 1,1-diethyl-3-(6-methyl-8β-ergolinyl)urea:
3-(2-bromo-6-methyl-8β-ergolinyl)-1,1-diethylurea; 81.4% yield, [α]$_D^{25}$=-70.0° (c=0.5, pyridine), hydrobromide; 82.8% yield, [α]$_D^{25}$=-42.0° (c=0.5, pyridine);
from 9,10-didehydro-6-methylergoline-8α-amine:
2-bromo-9,10-didehydro-6-methylergoline-8α-amine; 46.3% yield, mp 245° C. (decomposition) UV (methanol): λmax (ε)=227 (21,900); 241 (22,900); 303 nm (9,460 1/mol·cm)
from 6-methylergoline-8α-amine:
2-bromo-6-methylergoline-8α-amine; 68.7% yield, mp 242° C. (decomposition), [α]$_D^{25}$=-63.5° (c=0.5, pyridine);
from 9,10-didehydro-6-methylergoline-8α-carboxylic amide:
2-bromo-9,10-didehydro-6-methylergoline-8α-carboxylic acid amide; 55.0% yield, mp 213° C. (decomposition), [α]$_D^{25}$=+447° (c=0.5, pyridine);
from 6-methylergoline-8α-carboxylic acid amide:
2-bromo-6-methylergoline-8α-carboxylic acid amide, 78.0% yield, mp 248-252° C. (decomposition), [α]$_D^{25}$=-1.0° (c=0.5, pyridine);
from 9,10-didehydro-6-methyl-8β-ergoline carboxylic acid (1S)-(1-hydroxymethylethyl)amide hydrogen maleate (ergometrine hydrogen maleate):
2-bromoergometrine; 74.5% yield, mp 142° C. (decomposition), [α]$_D^{25}$=-13.8° (c=0.5, pyridine);
from 6-methyl-8α-ergolinecarboxylic acid (1S)-(1-hydroxy-methylethyl)amide (dihydroergometrine):
2-bromodihydroergometrine; 81.4% yield, mp 220-225° C. (decomposition), [α]$_D^{25}$=-131.8° (c=0.5, pyridine);
from (5'α)-12'-hydroxy-2'-methyl-5'-benzylergotamine-3',6',18-trione tartrate (ergotamine tartrate):
2-bromoergotamine; 68.0% yield, mp 195° C. (decomposition), [α]$_D^{25}$=-160.7° (c=0.5, chloroform) =-19.4° (c=0.5, pyridine);
from 9,10-dihydroergotamine:
2-bromo-9,10-dihydroergotamine; 76.2% yield, mp 199-201° C. (decomposition), [α]$_D^{25}$=-87.8° (c=0.5, pyridine); and
from (5'α)-12'-hydroxy-2'-(1-methylethyl)-5'-(2-methylpropyl)-ergotamine-3', 6',18-trione (α-ergocryptine):
2-bromo-α-ergocryptine; 73.5% yield, mp 213° C. (decomposition), [α]$_D^{25}$=-95.5° (c=0.5, pyridine) =-189.3° (c=0.5, chloroform).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

We claim:

1. A process for the selective preparation of a 2-bromo-8-ergolinyl compound of the formula

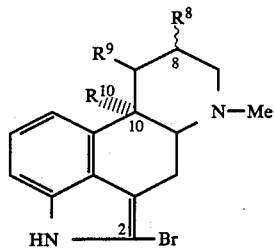

wherein
R$^8$ is NH$_2$, NH—CONEt$_2$, CONH$_2$

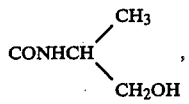

or

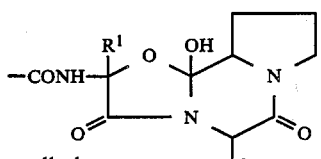

R$^1$ is C$_{1-4}$—alkyl,
R$^2$ is C$_{1-4}$—alkyl or benzyl,
R$^9$ and R$^{10}$ each are hydrogen or together form an additional C—C bond, and
the substituent R$^8$ is in the α-or β-position,
or an acid addition salt thereof,
comprising brominating by substitution in the 2-position the corresponding unbrominated 8-ergolinyl compound by reacting the latter with elemental bromine in the presence of hydrogen bromide in a compatible halogenated hydrocarbon solvent, so that bromination takes place regioselectively in the 2 position.

2. A method of claim 1, further comprising forming the acid addition salt of the product when it is not a 3. A method of claim 1, wherein R$^8$ is NH$_2$.
4. A method of claim 1, wherein R$^8$ is NH-CONEt$_2$.
5. A method of claim 1, wherein R$^8$ is CONH$_2$.
6. A method of claim 1, wherein R$^8$ is

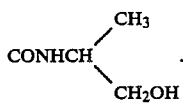

7. A method of claim 1, wherein R$^8$ is

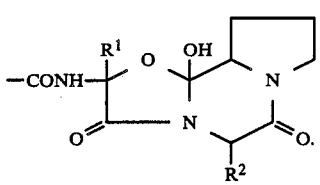

8. A method of claim 1, wherein R$^9$ and R$^{10}$ each are H.
9. A method of claim 1, wherein R$^9$ and R$^{10}$ together form an additional C—C bond.
10. A method of claim 1, wherein R$^8$ the group is in the α-position.
11. A method of claim 1, wherein the R$^8$ group is in the β-position.

12. A method of claim 1, wherein the solvent is methylene chloride, carbon tetrachloride, chloroform, 1,2-dichloroethane, 1,2-trichlorotrifluoroethane or methylene dichloride.

13. A method of claim 1, which is carried out under an inert gas atmosphere.

14. A method of claim 1, which is conducted at a compatible temperature below room temperature.

15. A method of claim 4, carried out at a temperature of 0-15° C.

16. A method of claim 1, wherein about from 1.0 to about 1.1 molar equivalents of bromine and from about 1.0 to about 1.1 molar equivalents of HBr are used, both based on the amount of ergolinyl compound.

17. The method of claim 1, wherein said hydrogen bromide is diluted in glacial acetic acid prior to addition to the reaction mexture.

18. A process for the preparation of a 2bromo-8-ergolinyl compound of the formula

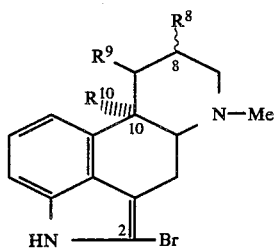

wherein $R^8$ is $NH_2$, $NH-CONEt_2$, $CONH_2$,

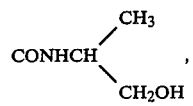

or

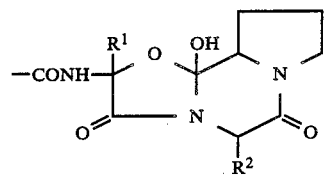

$R^1$ is $C_{1-4}$-alkyl, $R^2$ is $C_{1-4}$-alkyl or benzyl, $R^9$ and $R^{10}$ each are hydrogen or together form an additional C—C bond, and the substituent $R^8$ is in the α- or β-position, or an acid addition salt thereof, comprising brominating in the 2-position the corresponding unbrominated 8-ergolinyl compound by reacting the latter with elemental bromine in the presence of hydrogen bromide in a compatible halogenated hydrocarbon solvent, said solvent being methylene chloride, carbon tetrachloride, chloroform, 1,2-dichloroethane, 1,2-trichlorotrifluoroethane or methylene dichloride, wherein the process is carried out under an inert gas atmosphere, at a temperature of 0-15° C., and from about 1.0 to about 1.1 molar equivalents of HBr and bromine are used, both based on the amount of ergolinyl compound, said ergolinyl compound being present in a concentration of 0.01 to 0.2 molar.

* * * * *

UNITED STATES PATENT AND TRADEMARK OFFICE
CERTIFICATE OF CORRECTION

PATENT NO. : 4,970,314

DATED : November 13, 1990

INVENTOR(S) : Börner et al

It is certified that error appears in the above-identified patent and that said Letters Patent is hereby corrected as shown below:

Column 7, Claim 17, Line 20:

Reads: "to the reaction mexture."

Should Read: --to the reaction mixture.--

Column 7, Claim 18, Line 21:

Reads: "18. A process for the preparation of a 2bromo-8-"

Should Read: --18. A process for the preparation of a 2-bromo-8- --

Signed and Sealed this

Ninth Day of June, 1992

Attest:

DOUGLAS B. COMER

*Attesting Officer*    *Acting Commissioner of Patents and Trademarks*